US00PP08737P

United States Patent [19]

van Andel

[11] Patent Number: Plant 8,737

[45] Date of Patent: May 17, 1994

[54] ALSTROEMERIA NAMED STAPULA

[75] Inventor: Jacob van Andel, Aalsmeer, Netherlands

[73] Assignee: Van Staaveren B.V., Aalsmeer, Netherlands

[21] Appl. No.: 25,579

[22] Filed: Mar. 3, 1993

[51] Int. Cl.[5] ..... A01H 5/00

[52] U.S. Cl. ..... Plt./87.1

[58] Field of Search ..... Plt. 87.1

*Primary Examiner*—James R. Feyrer

*Attorney, Agent, or Firm*—Tilton, Fallon, Lungmus & Chestnut

[57] ABSTRACT

A new and distinctive Alstroemeria cultivar particularly distinguished by its profuse and recurrent production of very large sized flowers having six petals arranged in two concentric circles of three petals per flower; The new cultivar having magenta rose coloration for the body and phlox pink coloration for the base of its outer petals. The inside lateral petal having magenta rose and dresden yellow coloration for its body and phlox pink coloration for its base. The inner lateral petals also having numerous beetroot purple stripes and many chrysanthemum crimson spots. The inner median petal having a magenta rose body and a phlox pink base. The inner median petal having many beetroot stipes. These flowers being carried on erect stems branching from a tall main stem forming a strong upright bush.

1 Drawing Sheet

BACKGROUND OF THE NEW PLANT

This Alstroemeria cultivar originated as a seedling hybrid produced in my nursery at Aalsmeer, The Netherlands, by my crossing of two plants selected from a field of various Alstroemeria varieties maintained at my nursery for breeding purposes. This particular seedling was selected from those produced by the hybridization because of its bigger flowers and shorter growth period than an Alstroemeria named STALILAS (U.S. Plant Pat. NO. 5,207). This selected seedling was propagated by me at Aalsmeer by dividing root stock with very satisfactory results and thereafter this selected plant was propagated through several successive generations in the same manner which demonstrated conclusively that the novel characteristics of the originally selected seedling would be maintained from generation to generation and its homogeneity would be firmly established.

DESCRIPTION OF THE DRAWING

My new Alstroemeria plant is illustrated by the accompanying photographic drawing which, in full color, shows the form and coloration of the flowers as they appear with relatively close spacing at the upper end portion of the flowering stem of the plant. The colors shown are as nearly true to these herein specified as is reasonably possible to obtain by conventional photographic procedures.

DESCRIPTION OF THE NEW PLANT

The following is a detailed description of my new Alstroemeria plant as observed from plants grown under greenhouse conditions in Aalsmeer, The Netherlands, with the stated flower colors being according to The R.H.S. Colour Chart of The Royal Horticultural Society of London, England.

THE PLANT

Origin: Seedling.

Parentage:

*Seed parent.*—81 R 445-3 (unpatented). Pink color.

*Pollen parent.*—81 R 272-3 (unpatented). Pink color.

Both of these parent plants are so identified in my business records maintained at the office of my nursery at Aalsmeer, The Netherlands and the production of the aforementioned seedling are also recorded therein. Neither of the parent plants is commercially available.

Classification:

*Botanic.*—Alstroemeria hybrid.

*Commercial.*—Alstroemeria hybrid.

Form: An upright bush.

Height: About 130–180 cm.

Growth rate: Flowering in about 3–4 months following the first planting.

Main stem length: 150 cm.

Strength: Strong.

Branching character: The main stem has an umbel in which 4–6 branches (peduncles) are grouped. At the end of the peduncle a flower is situated on a pedicel. Above the peduncle additional pedicels may occur. The number of flowers per branch is 2–4.

Growth: Vigorous.

Foliage:

*Quantity.*—Abundant.

*Number of leaves.*—25–30.

*Size and shape of leaf.*—The leaf is elliptical shaped, about 14–18 cm in length and about 3–4 cm in width.

*Margin type.*—Smooth.

*Texture.*—Glossy.

*Color.*—Upper side — 137A. Under side — 137C.

Rhizomes: Yes.

*Color.*—RHS 155D.

*Size.*—10–30 cm.

THE BUD

Size:

*Diameter.*—1–2 cm.

*Length.*—2–3 cm.

Shape: Pear-shaped (long).

Rate of opening: Bud to flower in about 3–5 days.

Color of petals:

*When sepals first divide.*—RHS 64C.

*When petals begin to unfurl.*—RHS 64C.

Slitting: No.

THE FLOWER

Blooming habit: Recurrent and profuse — Spring and Fall.

Size of bloom: Very large.

*Diameter.*—6 cm.

*Depth.*—5 cm.

Borne: Singly.

Shape: When bloom first opens and when it matures the blooms are cup shaped.

Petalage:

*Number of petals.*—Six.

*Arrangement.*—Two concentric circles of three petals.

*Texture.*—Soft.

*Form.*—The two outer lateral petals are lobed at the apex and the top and inner petals are obovate.

*Margin type.*—The outer petals are generally smooth along the sides but finely dentate along the apical portion of the margin. The margins of the inner petals are substantially smooth.

*Apex.*—Pointed.

*Appearance.*—Velvety.

*Remain on stem.*—Three weeks.

*Color.*—Outer petals Body: RHS 64C. Base: RHS 62C. Reverse Side: RHS 64C. Inside lateral petals Body:RHS 64C/5B. Base:RHS 62C. Reverse side RHS:The body of the top two inner petals are RHS 64C in color with shadings of RHS 5B centrally over a central band of RHS 155D. The base is RHS 65D in color. The body of the third inner petal is also RHS 64C and the base is RHS 65A. The stripes are confined to the three inner petals and are RHS 59A in color. Spots: 30–40. Color: RHS 185A. Stripes: 40–50. Color: 71A. Inside median petal: Body: RHS 64C. Base: RHS:62B. Stripes: 25–30. Color: RHS 71A.

Discoloration after full bloom: Slightly.

Persistence: The petals of matured flowers do not hang on and dry.

Fragrance: None.

Lasting quality:

*On the plant.*—About 3 weeks.

*As a cut flower.*—About 2 weeks.

Flower stem:

*Length.*—About 6–8 cm.

*Character.*—Upright and strong.

*Color.*—RHS 137/C.

THE REPRODUCTIVE ORGANS

Stamens:

*Number.*—About six.

*Arrangement.*—Clustered around the style.

*Anthers.*—Size: 8–10 mm. Color: RHS 152A.

*Filaments.*—Length: About 5 cm. Color: RHS 63D.

*Pollen.*—Color: RHS 122B.

Pistils:

*Number.*—One.

*Styles.*—Length about 4–5 cm (RHS 64C/D).

*Stigmas.*—RHS 64C/D.

Fruit:

*Fertile.*—Yes.

*Shape.*—Round.

*Color.*—RHS 163A.

I claim:

1. A new and distinctive Alstroemeria plant, substantially as herein shown and described.

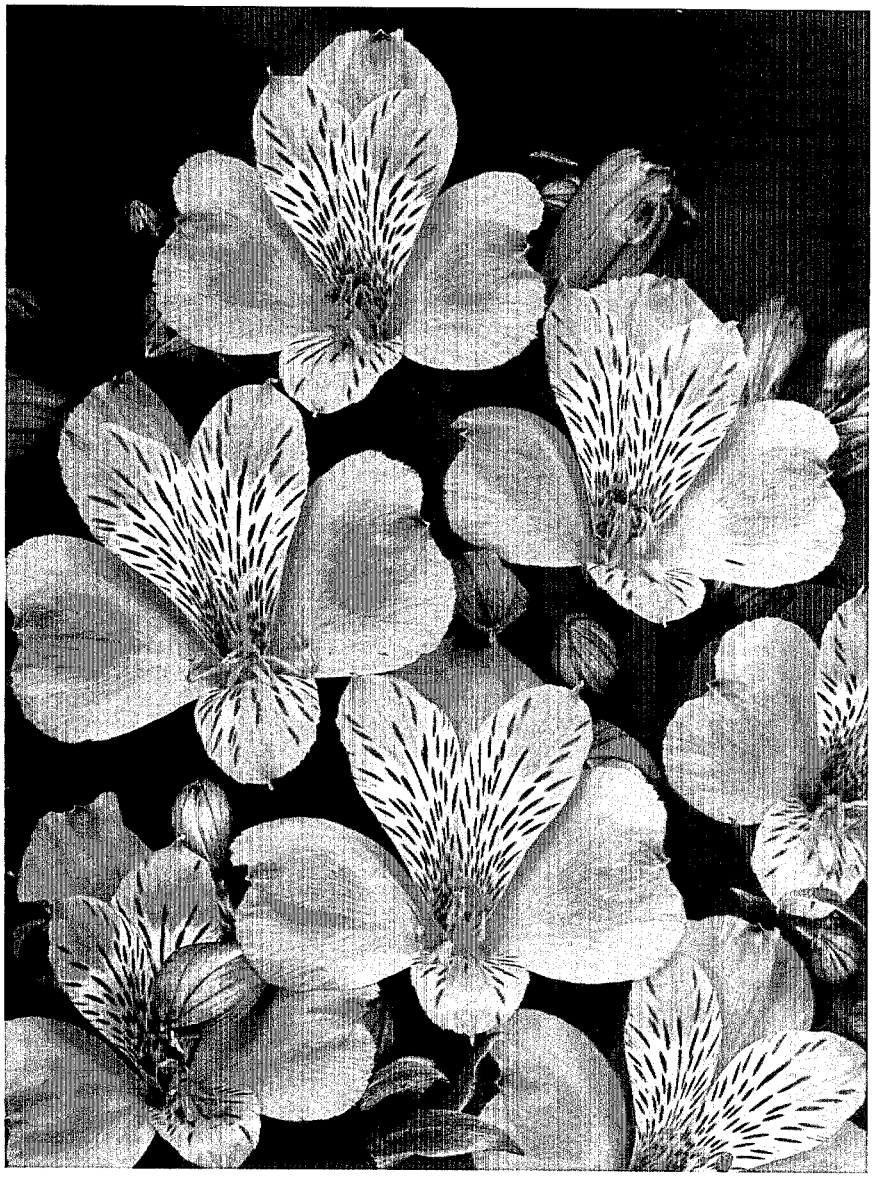

* * * * *